United States Patent [19]
Fassbind et al.

[11] Patent Number: 6,156,575
[45] Date of Patent: Dec. 5, 2000

[54] SAMPLE PROCESSING SYSTEM AND METHOD

[75] Inventors: Walter Fassbind, Baar; Emanuele Japichino, Sins; Werner Rey, Ebikon, all of Switzerland

[73] Assignee: Roche Diagnostic Corporation, Indianapolis, Ind.

[21] Appl. No.: 09/200,082

[22] Filed: Nov. 25, 1998

[51] Int. Cl.[7] .............................. G01N 35/00; B01L 3/14
[52] U.S. Cl. .............................. 436/50; 436/47; 436/180; 422/63; 422/65; 422/67; 422/100; 422/104; 235/375
[58] Field of Search ................... 422/63, 65, 67, 422/102, 103, 104; 436/43, 50, 47, 48, 49, 174, 180; 235/375, 383, 385, 486

[56] References Cited

U.S. PATENT DOCUMENTS

| | | | |
|---|---|---|---|
| 3,680,967 | 8/1972 | Engelhardt | 356/246 |
| 3,883,305 | 5/1975 | Hoskins et al. | 141/130 |
| 4,751,186 | 6/1988 | Baisch et al. | 436/47 |
| 4,877,134 | 10/1989 | Klein | 206/443 |
| 5,128,105 | 7/1992 | Berthold et al. | 422/104 |
| 5,663,545 | 9/1997 | Marquiss . | |
| 5,700,429 | 12/1997 | Buhler et al. | 422/104 |
| 5,735,387 | 4/1998 | Polaniec et al. | 198/690.1 |
| 5,777,303 | 7/1998 | Berney | 235/375 |

FOREIGN PATENT DOCUMENTS

| | | |
|---|---|---|
| 0 738 986 | 10/1996 | European Pat. Off. . |
| 2 107 510 | 5/1972 | France . |
| 2 135 854 | 12/1972 | France . |
| WO 96 07479 | 3/1996 | WIPO . |

OTHER PUBLICATIONS

Patent Abstracts of Japan vol. 017, No. 170 & JP 04 329360 A; Mar. 31, 1993; Nov. 18, 1992; Shimadzu Corp.

*Primary Examiner*—Maureen M. Wallenhorst
*Attorney, Agent, or Firm*—Gibbons, Del Deo Dolan, Griffinger & Vecchione

[57] ABSTRACT

An automatic sample processing system containing:
 a) a sample vessel,
 b) a sample vessel carrier having a chamber to receive the sample vessel, and
 c) a sample identification component which carries a readable identification of a sample. The sample identification component is removably attachable to the sample vessel and to the sample vessel carrier.

8 Claims, 2 Drawing Sheets

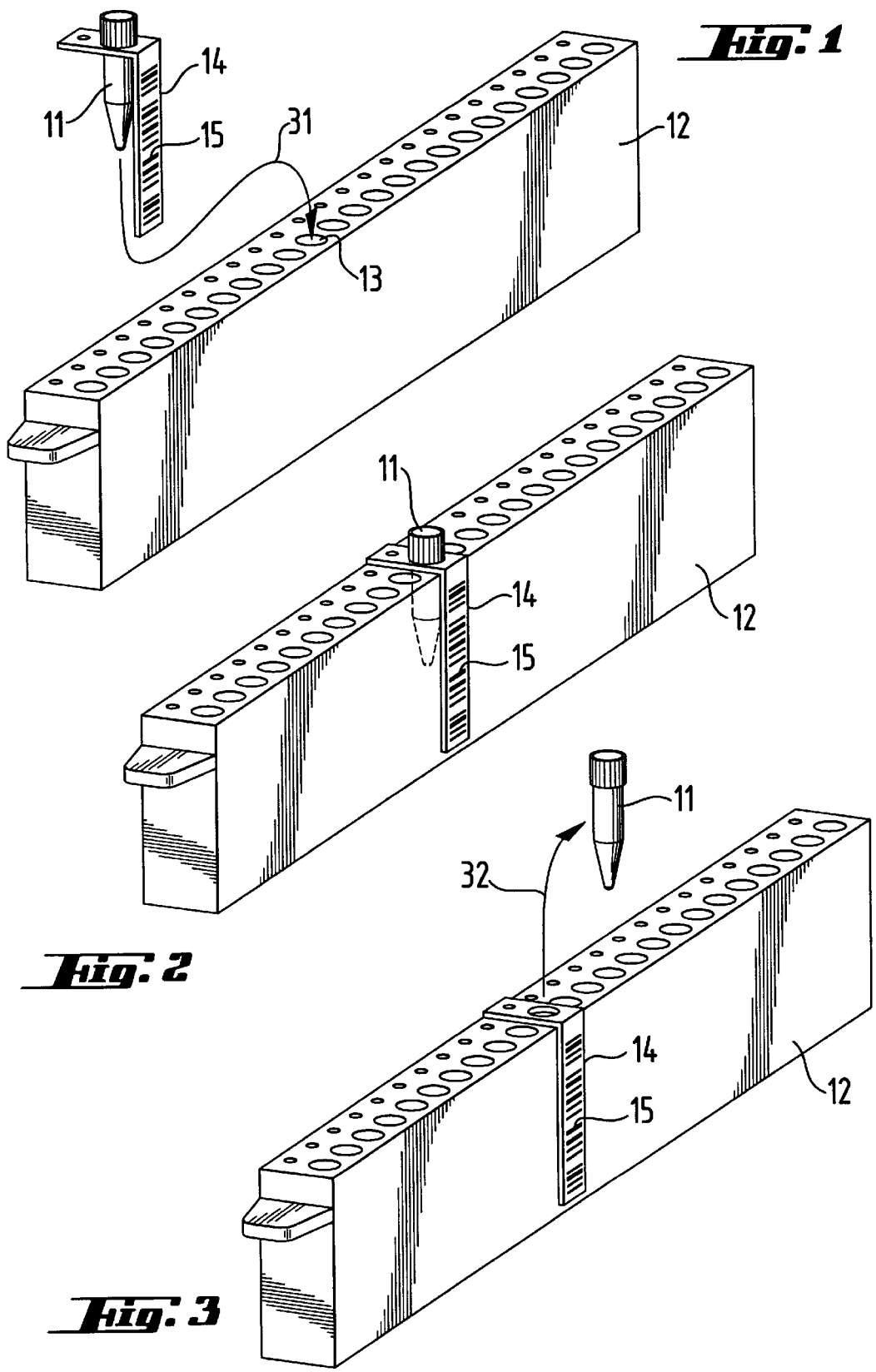

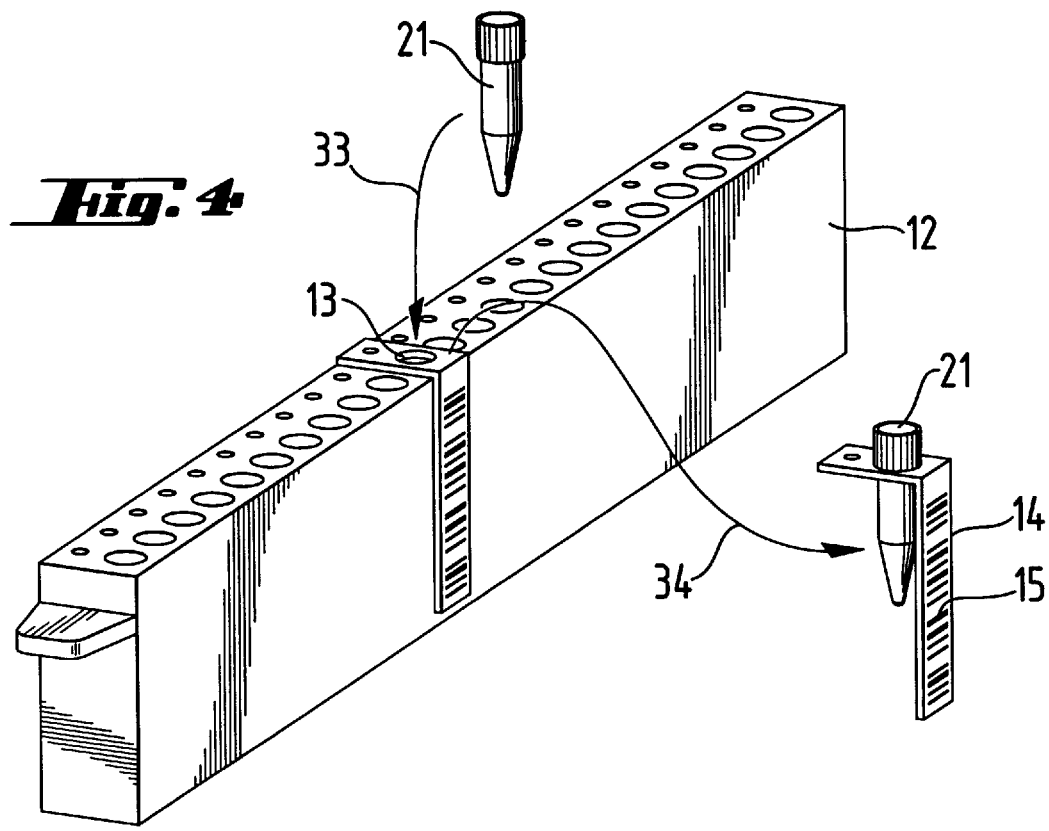
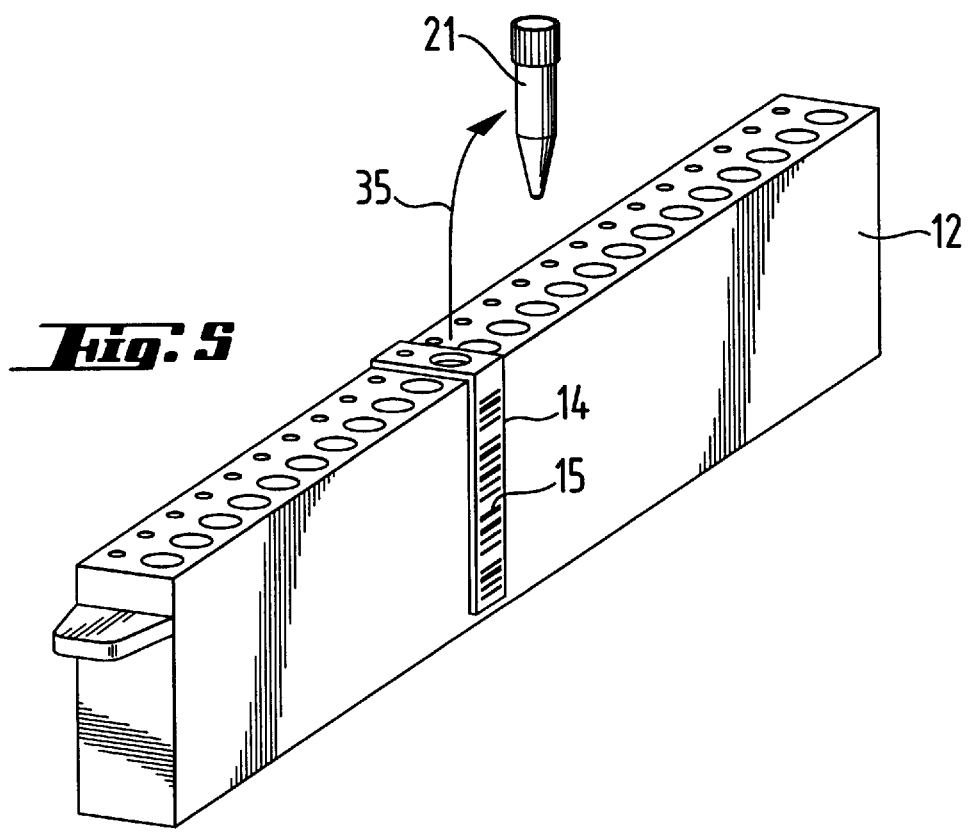

SAMPLE PROCESSING SYSTEM AND METHOD

FIELD OF THE INVENTION

The present invention concerns an automatic sample processing system.

The invention further concerns a method for sample identification in an automatic sample processing system.

The invention concerns in particular an automatic system for processing cell material samples to isolate nucleic acids contained in that sample.

BACKGROUND OF THE INVENTION

Reliable sample identification is indispensable in automatic sample processing systems and has to be ensured at various stages of the sample processing, including sample collection, at which a sample taken from a patient is introduced into a primary sample tube; splitting of that primary sample into a number of portions which are each transferred to respective sample vessels which enter an automatic sample processing system as input sample vessels; and delivery of processed samples derived from said primary sample in output sample vessels.

The reliability of sample identification, by carefully labeling each sample vessel properly at every processing step, requires a considerable amount of labor and material, particularly in processes involving numerous and diverse processing steps. Moreover a considerable amount of manual handling increases the probability of error and is therefor in itself an obstacle to reliable sample identification.

A main aim of the invention is therefore to provide a system and a method which provides highly reliable sample identification with a reduced amount of handling and material required.

SUMMARY OF THE INVENTION

According to the invention this aim is obtained with an automatic sample processing system comprising a) a sample vessel having no identification on it, b) a sample vessel carrier having a chamber to receive said sample vessel, and c) a sample identification component which carries on it a readable identification of a sample contained in, or to be pipetted into, said sample vessel, said sample identification component being configured and dimensioned to be removably attachable to said sample vessel and also to said sample vessel carrier at a position thereof which corresponds to the position of the chamber which receives said sample vessel, said sample identification component being adapted to remain attached to said sample vessel carrier when said sample vessel is removed from said sample vessel carrier.

According to another aspect of the invention the above indicated aim is obtained with a method for sample identification in an automatic sample processing system, said method comprising a) using a sample vessel having no identification on it, b) using a sample vessel carrier having a chamber apt to receive said sample vessel, c) removably attaching a sample identification component to said sample vessel, before positioning it on said sample vessel carrier, said sample identification component carrying on it a readable identification of a sample contained in or to be pipetted into said sample vessel, d) positioning said sample vessel in said chamber of the sample vessel carrier and thereby removably attaching its sample identification component also to said sample vessel carrier at a position thereof which corresponds to the position of said chamber which receives the sample vessel, and e) transporting said sample vessel without sample identification component attached to it from its position on the sample vessel carrier to a sample vessel processing position located outside of the carrier, said sample identification component remaining attached to said sample vessel carrier.

The main advantage of a system and a method according to the invention is that a highly reliable sample identification is obtained with a minimum of handling and material requirements.

BRIEF DESCRIPTION OF THE DRAWINGS

FIG. 1 shows a sample vessel and sample identification component approaching a sample vessel carrier.

FIG. 2 shows a sample vessel within a chamber of the carrier, and the sample identification component attached to the carrier.

FIG. 3 shows the sample identification component remaining attached to the carrier as the sample vessel is removed.

FIG. 4 shows a second sample vessel being returned to the chamber where the sample identification component is attached, followed by the sample vessel and sample identification component being removed together.

FIG. 5 shows a second sample vessel being removed from the sample vessel carrier while the sample identification component remains attached to the carrier.

DETAILED DESCRIPTION OF THE INVENTION

Exemplified embodiments of the invention are described below with reference to the accompanying drawings wherein FIGS. 1 to 5 show schematic perspective views of components of a system according to the invention and illustrate method steps carried out with those components.

EXAMPLE 1

As shown by FIG. 1 a first embodiment of an automatic sample processing system according to the invention comprises a sample vessel 11 having no identification on it, a sample vessel carrier 12 having a chamber 13 adapted to receive sample vessel 11, and a sample identification component 14. Sample identification component 14 carries on it a readable identification 15 of a sample contained in or to be pipetted into sample vessel 11. Sample identification component 14 is configured and dimensioned to be removably attachable to sample vessel 11 and also to sample vessel carrier 12 at a position thereof which corresponds to the position of the chamber 13 which receives sample vessel 11. Sample identification component 14 is further configured and dimensioned to remain attached to sample vessel carrier 12 when sample vessel 11 is removed from sample vessel carrier 12.

A method according to the invention carried out with the first embodiment just described comprises the following steps illustrated by FIGS. 1 to 3:

(1) attaching removable sample identification component 14 to sample vessel 11 as shown by FIG. 1, before positioning it in chamber 13 of sample vessel carrier 12, (2) positioning sample vessel 11 in chamber 13 of the sample vessel carrier 12 as shown by FIGS. 1 and 2 (in FIG. 1 arrow 31 represents the path followed by sample vessel 11 when it is moved towards chamber 13) and thereby attaching removable sample identification component 14 also to sample vessel carrier 12 at a position thereof which corresponds to the position of chamber 13 which receives sample vessel 11 (as shown by FIG. 2), and (3) transporting sample vessel 11 as shown by FIG. 3 (in FIG. 3 arrow 32 represents the path followed by sample vessel 11 when it is moved away from chamber 13), without sample identification component 14 attached to it, from its position on the sample vessel carrier 12 to a sample vessel processing position (not shown in the figures) located outside of the latter carrier, sample identification component 14 remaining attached to sample vessel carrier 12.

EXAMPLE 2

As shown by FIGS. 1 to 4 a second embodiment of an automatic sample processing system according to the invention comprises a first sample vessel 11 and a second sample vessel 21 which have no identification on them, a sample vessel carrier 12 having a chamber 13 adapted to receive alternatively either first sample vessel 11 or second sample vessel 21, and a sample identification component 14. Sample identification component 14 carries on it a readable identification 15 of a sample contained in, or to be pipetted into, the first sample vessel 11, and of a sample contained in, or to be pipetted into, second sample vessel 21. The sample contained in or to be pipetted into the second sample vessel 21 is obtained by processing a portion of the sample contained in the first sample vessel 11. Sample identification component 14 is configured and dimensioned to be removably attachable to first sample vessel 11, to second sample vessel 21, and also to sample vessel carrier 12 at a position thereof which corresponds to the position of the chamber 13 which receives a sample vessel. Sample identification component 14 is further so configured and dimensioned to remain attached to sample vessel carrier 12 when first sample vessel 11 or second sample vessel 21 is removed from sample vessel carrier 12.

A method according to the invention carried out with the second embodiment just described comprises the following steps illustrated by FIGS. 1 to 4:

(1) attaching removable sample identification component 14 to first sample vessel 11 as shown by FIG. 1, before positioning it on sample vessel carrier 12, (2) positioning first sample vessel 11 in chamber 13 of sample vessel carrier 12 as shown by FIGS. 1 and 2 (in FIG. 1 arrow 31 represents the path followed by sample vessel 11 when it is moved towards chamber 13) and thereby removably attaching its sample identification component 14 also to sample vessel carrier 12 at a position thereof which corresponds to the position of chamber 13 which receives first sample vessel 11 (as shown by FIG. 2), (3) transporting first sample vessel 11 as shown by FIG. 3 (in FIG. 3 arrow 32 represents the path followed by sample vessel 11 when it is moved away from chamber 13) without sample identification component 14 attached to it from its position on sample vessel carrier 12 to a first sample vessel processing position (not shown in the figures) located outside of carrier 12 in order to obtain a processed sample, sample identification component 14 remaining attached to sample vessel carrier 12, (4) transferring the processed sample from the sample processing device where said processed sample is obtained to a second sample vessel 21 positioned at a second sample vessel processing position (not shown in the figures) located outside of the sample vessel carrier 12, and (5) transporting second sample vessel 21 as shown by FIG. 4 (in FIG. 4 arrow 33 represents the path followed by sample vessel 21 when it is moved towards chamber 13) from the second sample vessel processing position to the position formerly occupied by first sample vessel 11 on the sample vessel carrier 12, the processed sample contained in second sample vessel 21 being thereby identified by sample identification component 14 located at the latter position on the sample vessel carrier 12.

In a preferred embodiment of the method just described a single sample vessel processing position is used as the first sample vessel processing position and also as the second sample vessel processing position.

After step (5) of the method described above, second sample vessel 21 containing the processed sample can be handled further in one of the following ways, either according to step (6.1) or to (6.2) described hereinafter with reference to FIGS. 4 and 5:

(6.1) Second sample vessel 21 with sample identification component 14 attached to it is transported as shown by FIG. 4 (in FIG. 4 arrow 34 represents the path followed by second sample vessel 21 when it is moved away from chamber 13) from its position on sample vessel carrier 12 to a further processing station (not shown in the figures) located outside of carrier 12. Such a processing station can be e.g. an automatic analyzer including means for identifying the sample carried by sample vessel 21 by machine reading of the identification 15 carried by sample identification component 14 attached to sample vessel 21.

(6.2) Second sample vessel 21 without sample identification component 14 attached to it is transported as shown by FIG. 5 (in FIG. 5 arrow 35 represents the path followed by second sample vessel 21 when it is moved away from chamber 13) from its position on sample vessel carrier 12 to a further processing station located outside of carrier 12. Such a processing station can be e.g. an automatic analyzer where sample vessel 21 is automatically positioned at a predetermined position assigned to sample vessel 21 on the basis of information obtained e.g. by machine reading of the identification 15 carried by sample identification component 14 attached to sample vessel 21 and transmission of that information to the analyzer.

EXAMPLE 3

As described hereinafter with reference to FIGS. 1 to 3, a third embodiment of an automatic sample processing system according to the invention comprises a sample vessel carrier 12 having a plurality of chambers 13, a plurality of sample vessels 11 having no identification on them (for simplicity only one of such vessels is represented in FIGS. 1–3), each of the chambers 13 of sample vessel carrier 12 being adapted to receive one of the sample vessels 11, and a plurality of sample identification components 14. Each of sample identification components 14 carries on it a readable identification 15 of a sample contained in or to be pipetted into one of sample vessels 11. Each of sample identification components 14 is configured and dimensioned to be removably attachable to one of sample vessels 11 and also to sample vessel carrier 12 at a position thereof which corresponds to the position of the chamber 13 which receives sample vessel.

Each of sample identification components 14 is further so configured and dimensioned to remain attached to sample carrier 12 when the corresponding sample vessel is removed from sample vessel carrier 12.

A method according to the invention carried out with the third embodiment just described comprises the following steps described hereinafter with reference to FIGS. 1 to 3:

(1) attaching a removable sample identification component 14 to each of sample vessels 11 as shown by FIG. 1, before positioning it on sample vessel carrier 12, (2) positioning each of sample vessels 11 in one of chambers 13 of the sample vessel carrier 12 as shown by FIGS. 1 and 2 and thereby removably attaching its respective sample identification component 14 also to sample vessel carrier 12 at a position thereof which corresponds to the position of the chamber 13 which receives the corresponding sample vessel as shown by FIG. 2, and (3) transporting each of sample vessels 11 as shown by FIG. 3 without sample identification component 14 attached to it from its position on the sample vessel carrier 12 to a sample vessel processing position (not shown in the figures) located outside of the latter carrier 12, the sample identification components 14 of the transported vessels 11 remaining attached to sample vessel carrier 12.

EXAMPLE 4

As described hereinafter with reference to FIGS. 1 to 3, a fourth embodiment of an automatic sample processing system according to the invention comprises a plurality of first sample vessels 11 and a plurality of second sample vessels 21, which first and second sample vessels have no identification on them, a sample vessel carrier 12 having a plurality of chambers 13, each chamber 13 being apt to receive alternatively either one first sample vessels 11 or one of second sample vessels 21, and a plurality of sample identification components 14, each of which carries on it a readable identification 15 of a sample contained in or to be pipetted into one of first sample vessels 11 or one of second sample vessels 21. Each sample contained or to be pipetted into one of second vessels 21 is obtained by processing a portion of the sample contained in a corresponding first sample vessel 11. Each sample identification component 14 is configured and dimensioned to be removably attachable to one of first sample vessels 11, to one of second sample vessels 21, and also to sample vessel carrier 12 at a position thereof which corresponds to the position of the chamber 13 which receives a first sample vessel 11 or a second sample vessel 21. Each sample identification component 14 is further so configured and dimensioned to remain attached to sample carrier 12 when the corresponding sample vessel is removed from sample vessel carrier 12.

A method according to the invention carried out with the fourth embodiment just described comprises the following steps described hereinafter with reference to FIGS. 1 to 4:

(1) attaching a removable sample identification component 14 to each of first sample vessels 11 as shown by FIG. 1, before positioning it on sample vessel carrier 12, (2) positioning each of first sample vessels 11 in one of chambers 13 of sample vessel carrier 12 as shown by FIGS. 1 and 2 and thereby removably attaching its sample identification component 14 also to sample vessel carrier 12 at a position thereof which corresponds to the position of the chamber 13 which receives the corresponding first sample vessel, (3) transporting each of first sample vessels 11 as shown by FIG. 3 without sample identification component 14 attached to it from its position on sample vessel carrier 12 to a first sample vessel processing position located outside of the latter carrier 12 in order to obtain a processed sample, the sample identification component 14 of the transported sample vessel remaining attached to sample vessel carrier 12, (4) transferring each of processed samples from sample processing device to a second sample vessel 21 positioned at a second sample vessel processing position located outside of the sample vessel carrier 12, and (5) transporting each of second sample vessels 21 as shown by FIG. 4 from second sample vessel processing position to the position formerly occupied by the corresponding first sample vessel 11 on sample vessel carrier 12, the sample contained in each of second sample vessels 21 being thereby identified by the sample identification component 14 located at the latter position on the sample vessel carrier 12.

In a preferred embodiment of the method just described a single sample vessel processing position is used as first sample vessel processing position and also as second sample vessel processing position.

After step (5) of the method described above, each of the second sample vessels 21 containing the processed sample can be handled further in one of the following ways, either according to step (6.1a) or to (6.2a) described hereinafter with reference to FIGS. 4 and 5:

(6.1a) Each of the second sample vessels 21 with sample identification component 14 attached to it is transported as shown by FIG. 4 (in FIG. 4 arrow 34 represents the path followed by second sample vessel 21 when it is moved away from chamber 13) from its position on sample vessel carrier 12 to a further processing station (not shown in the figures) located outside of carrier 12. Such a processing station can be e.g. an automatic analyzer including means for identifying the sample carried by sample vessel 21 by machine reading of the identification 15 carried by sample identification component 14 attached to sample vessel 21.

(6.2a) Each of the second sample vessels 21 without sample identification component 14 attached to it is transported as shown by FIG. 5 (in FIG. 5 arrow 35 represents the path followed by second sample vessel 21 when it is moved away from chamber 13) from its position on sample vessel carrier 12 to a further processing station located outside of carrier 12. Such a processing station can be e.g. an automatic analyzer where sample vessel 21 is automatically positioned at a predetermined position assigned to sample vessel 21 on the basis of information obtained e.g. by machine reading of the identification 15 carried by sample identification component 14 attached to sample vessel 21 and transmission of that information to the analyzer.

In all examples described above the sample vessels 11 and 21, the sample vessel carrier 12 and the sample identification component 14 are preferably made of suitable plastic materials. The readable identification 15 on sample identification component 14 is preferably a barcode label.

What is claimed is:

1. An automatic sample processing system comprising
 a) a first sample vessel and a second sample vessel,
 b) a sample vessel carrier having a chamber adapted to receive alternatively either said first sample vessel or said second sample vessel, and
 c) a sample identification component, which carries a readable identification of a sample contained in, or to be pipetted into, the first sample vessel and of a sample contained in, or to be pipetted into, said second sample vessel, said sample contained in, or to be pipetted into, the second sample vessel being obtained by processing a portion of the sample contained in the first sample vessel, and said sample identification component being removably attachable to said first sample vessel, to said second sample vessel, and also to said sample vessel carrier at a position thereof which corresponds to the position of the chamber which receives a sample vessel, said sample identification component being adapted to remain attached to said sample vessel carrier when said first sample vessel or said second sample vessel is removed from said sample vessel carrier.

2. A method for sample identification in an automatic sample processing system comprising a) providing a sample vessel, b) providing a sample vessel carrier having a chamber adapted to receive said sample vessel, c) removably attaching a sample identification component to said sample vessel, before positioning it on said sample vessel carrier, said sample identification component carrying on it a readable identification of a sample contained in or to be pipetted into said sample vessel, d) positioning said sample vessel in said chamber of the sample vessel carrier and thereby removably attaching its sample identification component also to said sample vessel carrier at a position thereof which corresponds to the position of said chamber which receives the sample vessel, and e) transporting said sample vessel without said sample identification component attached to it from its position on the sample vessel carrier to a sample vessel processing position located outside of said sample vessel the latter carrier, said sample identification component remaining attached to said sample vessel carrier.

3. A method for sample identification in an automatic sample processing system comprising a) providing a first sample vessel and a second sample vessel, b) providing a sample vessel carrier having a chamber adapted to receive alternatively either said first sample vessel or said second sample vessel, c) removably attaching a sample identification component to said first sample vessel, before positioning it on said sample vessel carrier, said sample identification component carrying on it a readable identification of a sample contained in, or to be pipetted into said first sample vessel, d) positioning said first sample vessel in said chamber of said sample vessel carrier and thereby removably attaching its sample identification component also to said sample vessel carrier at a position thereof which corresponds to the position of said chamber which receives said first sample vessel, e) transporting said first sample vessel without sample identification component attached to it from its position on said sample vessel carrier to a first sample vessel processing position located outside of said sample vessel carrier, said sample identification component remaining attached to said sample vessel carrier, f) processing the sample contained in the first sample vessel in a sample processing device to obtain a processed sample therefrom, g) transferring said processed sample from said sample processing device to a second sample vessel positioned at a second sample vessel processing position located outside of the sample vessel carrier, and h) transporting said second sample vessel from said second sample vessel processing position to the position formerly occupied by said first sample vessel on the sample vessel carrier, the processed sample contained in said second sample vessel being thereby identified by said sample identification component located at the latter position on the sample vessel carrier.

4. A method according to claim 3, wherein a single sample vessel processing position is used as first sample vessel processing position and also as second sample vessel processing position.

5. An automatic sample processing system comprising a) a plurality of first sample vessels, and a plurality of second sample vessels, b) a sample vessel carrier having a plurality of chambers, each chamber being adapted to receive alternatively either one of said first sample vessels or one of said second sample vessels, and c) a plurality of sample identification components, each of said components carrying on it a readable identification of a sample contained in, or to be pipetted into, one of said first sample vessels or one of said second sample vessels, said sample contained or to be pipetted into one of said second vessels being obtained by processing a portion of the sample contained in a corresponding first sample vessel, and said sample identification component being removably attachable to one of said first sample vessels, to one of said second sample vessels, and also to said sample vessel carrier at a position thereof which corresponds to the position of the chamber which receives a first sample vessel or a second sample vessel, each of said sample identification components being adapted to remain attached to said sample vessel carrier when the corresponding sample vessel is removed from said sample vessel carrier.

6. A method for sample identification in an automatic sample processing system comprising a) providing a plurality of sample vessels, b) providing a sample vessel carrier having a plurality of chambers, each chamber being adapted to receive one of said sample vessels, c) removably attaching a sample identification component to each of said sample vessels, before positioning it on said sample vessel carrier, said sample identification component carrying a readable identification of a sample contained in or to be pipetted into a sample vessel, d) positioning each of said sample vessels in one of said chambers of the sample vessel carrier and thereby removably attaching a respective sample identification component also to said sample vessel carrier at a position thereof which corresponds to the position of the chamber which receives the corresponding sample vessel, and e) transporting each of said sample vessels without sample identification component attached from its position on the sample vessel carrier to a sample vessel processing position located outside of said sample vessel carrier, the sample identification components of the transported vessels remaining attached to said sample vessel carrier.

7. A method for sample identification in an automatic sample processing system comprising
   a) providing a plurality of first sample vessels and a plurality of second sample vessels,
   b) using a sample vessel carrier having a plurality of chambers, each of said chambers being adapted to receive alternatively either one of said first sample vessels or one of said second sample vessels, and
   c) removably attaching a sample identification component to each of said first sample vessels, before positioning it on said sample vessel carrier, said sample identification component carrying a readable identification of a sample contained in, or to be pipetted into, one of said first sample vessels,
   d) positioning each of said first sample vessels in one of said chambers of said sample vessel carrier and thereby removably attaching its sample identification component to said sample vessel carrier at a position thereof which corresponds to the position of the chamber which receives the corresponding first sample vessel,
   e) transporting each of said first sample vessels without sample identification component attached to it from its position on said sample vessel carrier to a first sample vessel processing position located outside of said sample vessel carrier, the sample identification component of the transported sample vessel remaining attached to said sample vessel carrier,
   f) processing the sample contained in each of the transported first sample vessels in a sample processing device to obtain a processed sample therefrom,
   g) transferring each of said processed samples from said sample processing device to a second sample vessel positioned at a second sample vessel processing position located outside of the sample vessel carrier, and
   h) transporting each of said second sample vessels from said second sample vessel processing position to the position formerly occupied by the corresponding first sample vessel on said sample vessel carrier, the sample contained in each of said second sample vessels being thereby identified by the sample identification component located at the latter position on the sample vessel carrier.

8. A method according to claim 7, wherein a single sample vessel processing position is used as first sample vessel processing position and also as second sample vessel processing position.

* * * * *